US006913896B1

(12) United States Patent
Raven et al.

(10) Patent No.: US 6,913,896 B1
(45) Date of Patent: Jul. 5, 2005

(54) ASSAY WITH REDUCED BACKGROUND

(75) Inventors: Neil David Hammond Raven, Salisbury (GB); Matthew Patrick Wictome, Salisbury (GB)

(73) Assignee: Health Protection Agency, Salisbury (GB)

( * ) Notice: Subject to any disclaimer, the term of this patent is extended or adjusted under 35 U.S.C. 154(b) by 0 days.

(21) Appl. No.: 09/889,520

(22) PCT Filed: Feb. 3, 2000

(86) PCT No.: PCT/GB00/00315

§ 371 (c)(1),
(2), (4) Date: Dec. 10, 2001

(87) PCT Pub. No.: WO00/46357

PCT Pub. Date: Aug. 10, 2000

(30) Foreign Application Priority Data

Feb. 5, 1999 (GB) .............................. 9902659

(51) Int. Cl.[7] .......................................... G01N 33/543
(52) U.S. Cl. ........................ 435/7.92; 435/7.1; 435/4; 435/183; 435/184; 435/188.5; 435/194; 436/518; 436/175
(58) Field of Search .............................. 435/7, 4, 183, 435/184, 188.5, 194; 436/518, 175

(56) References Cited

U.S. PATENT DOCUMENTS

| | | | | |
|---|---|---|---|---|
| 4,385,120 A | * | 5/1983 | Atkinson et al. | 435/194 |
| 4,584,272 A | | 4/1986 | Imahori et al. | 435/194 |
| 4,628,031 A | * | 12/1986 | Zeikus et al. | 435/205 |
| 4,656,128 A | | 4/1987 | Chlebowski et al. | 435/7 |

FOREIGN PATENT DOCUMENTS

| | | |
|---|---|---|
| EP | 0 089 210 A2 | 9/1983 |
| EP | 0 304 934 A2 | 3/1989 |
| WO | WO 94/06933 | 3/1994 |
| WO | WO 96/02666 | 2/1996 |
| WO | WO 97/10505 | 3/1997 |

OTHER PUBLICATIONS

Murakami et al, Bioluminescent enzyme immunoassay using thermostable mutant luciferase and acetate kinase as a labelled enzyme, 1998, Analytica Chimica ACTA, vol. 361, pp. 19–26.*
International Search Report for PCT/GB00/00315, mailed Jun. 26, 2000.
Beards, G.M., "Endogenous alkaline phosphatase is a cause of non–specific reactions in enzyme–immunoassays for rotavirus based on alkaline phosphatase conjugates," *Med. Lab. Sci.* 45:97–98, Blackwell Science Limited (1988).
Corning, ELISA Technical Bulletin #3, accessed Nov. 29, 2000 at <http://www.scienceproducts.corning.com/techinfo/publications/bull_3.html>.

(Continued)

*Primary Examiner*—James Housel
*Assistant Examiner*—Deborah A. Davis
(74) *Attorney, Agent, or Firm*—Sterne, Kessler, Goldstein & Fox P.L.L.C.

(57) ABSTRACT

In as assay, an analyte is specifically associated with a reporter adenylate kinase, ADP is added and then formation of ATP is monitored. Prior to addition of ADP, adenylate kinase other than reporter adenylate kinase is removed. Assay apparatus comprises a solid phase on which is immobilised the analyte or an antibody specific for the analyte, a reporter composition comprising a thermostable adenylate kinase coupled to an antibody specific for the analyte, and ADP plus associated reagents for conversion of ADP into ATP by thermostable adenylate kinase.

10 Claims, 4 Drawing Sheets

OTHER PUBLICATIONS

Corning, ELISA Technical Bulletin #4, accessed Nov. 29, 2000 at <http://www.scienceproducts.corning.com/techinfo/publications/bull_4.html>.

Ekins, R.P., "Chapter 9, Immunoassay Design and Optimisation," in *Principles and Practice of Immunoassay*, Price, C.P and Newman, D.J., Eds., Stockton Press, New York, NY, pp. 203–205 (1997).

Fragoso, G. et al., "Immunoenzymatic Assay That Measures the Expression of Murine Histocompatibility Antigens in Macrophages and Lymphocytes," *J. Clin. Lab. Anal.* 7:348–352, Wiley–Liss, Inc. (1993).

Holzmann, B. and Johnson, J.P., "A Beta–Galactosidase Linked Immunoassay for the Analysis of Antigens on Individual Cells," *J. Immunol. Meth.* 60:359–367, Elsevier Science Publishers B.V. (1983).

Kim, J.G. et al., "A Biotin–Streptavidin Enzyme Immunoassay for Detection of Antibodies to Porcine Granulosa Cell Antigens," *J. Immunoassay* 12:447–464, Marcel Dekker, Inc. (1991).

Morris, R.E. and Horowitz, D.A., "Cellular Enzyme–Linked Immunospecific Assay (CELISA). IV. Inhibition of Endogenous Cellular Alkaline Phosphatase Activity," *J. Immunol. Meth.* 68:11–17, Elsevier Science Publishers B.V. (1984).

Perera, V.Y. et al., "Nylon Bead Enzyme–Linked Immunosorbent Assay for Detection of Sub–Picogram Quantities of Brucella Antigens," *J. Clin. Microbiol.* 18:601–608, American Society for Microbiology (1983).

Swanson, N.R. et al., "An Enzyme–Linked Immunosorbent Assay for the Detection of Hepatocyte Plasma Membrane Antibodies," *J. Immunol. Meths.* 85:203–216, Elsevier Science Publishers B.V. (1985).

Tijssen, P., "Practice and Theory of Enzyme Immunoassays," in *Laboratory Techniques in Biochemistry and Molecular Biology*, Burdon, R.H. and van Knippenberg, P.H., Eds., Elsevier Science Publishers B.V., Amsterdam, The Netherlands, pp. 132–136 (1985).

* cited by examiner

FIG. 1 Prion ELISA - 1
*1. Blocking*
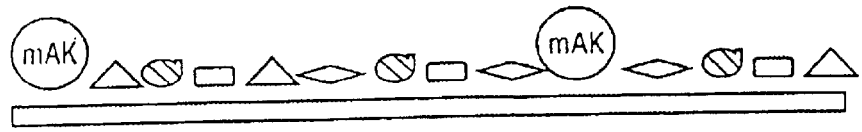
*2. Antibody binding*
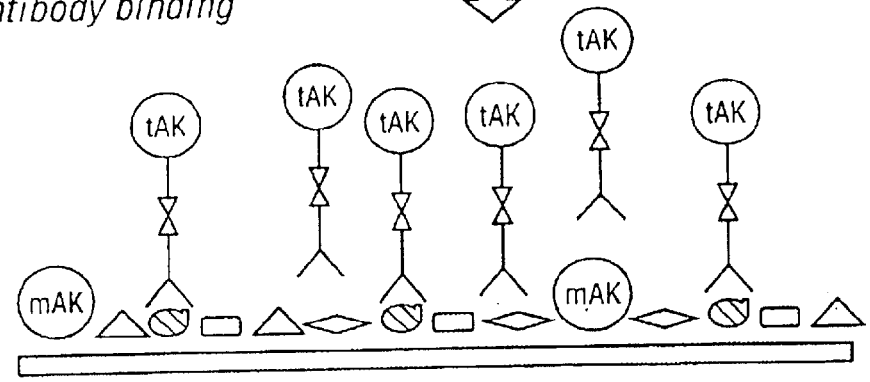
*3. Washing*
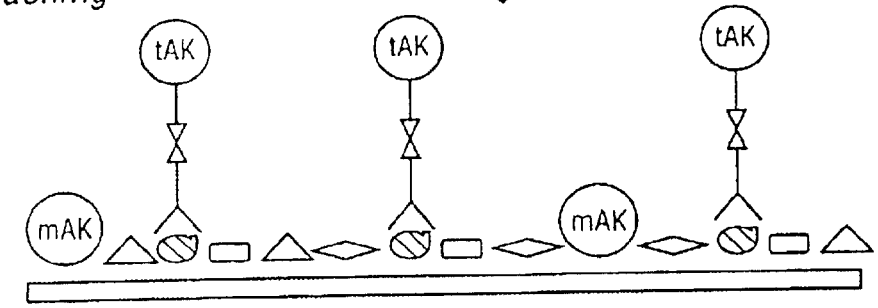
*4. Linker cleavage*
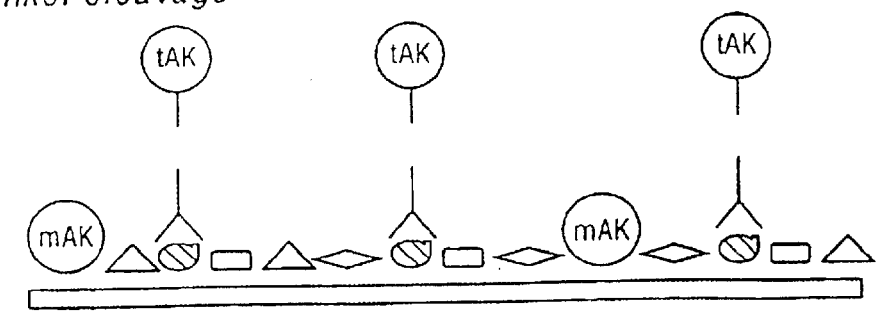

FIG. 2    Prion ELISA - 2
5. Recovery / Transfer
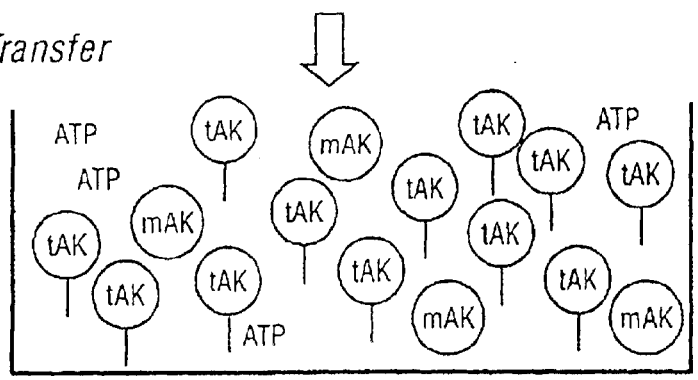
6. Thermal Inactivation
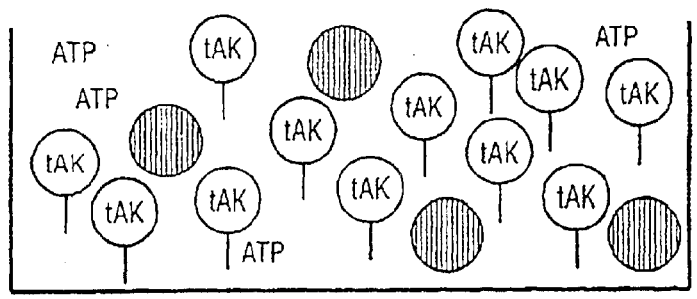
7. ATP Hydrolysis
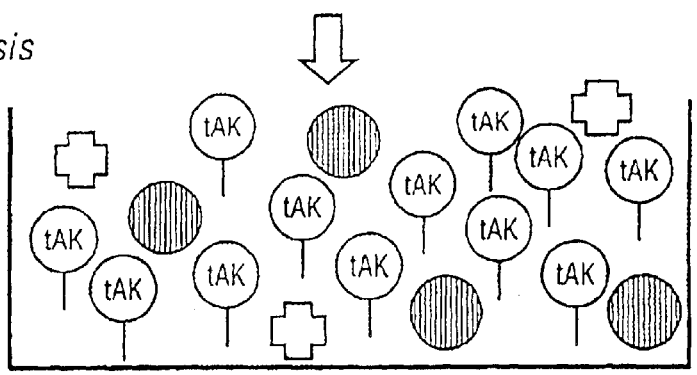
8. Thermal Inactivation
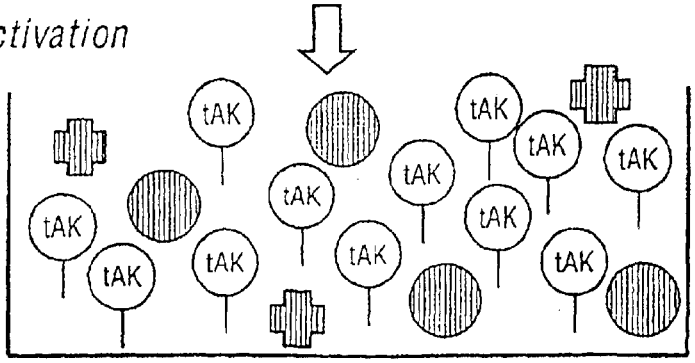

FIG. 3 Prion ELISA - 3
*9. ATP Generation*
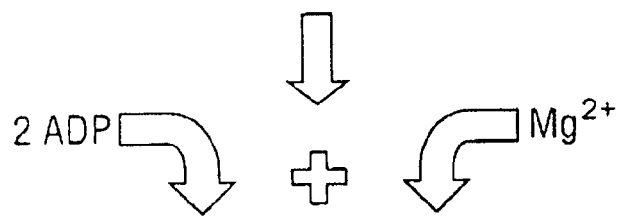
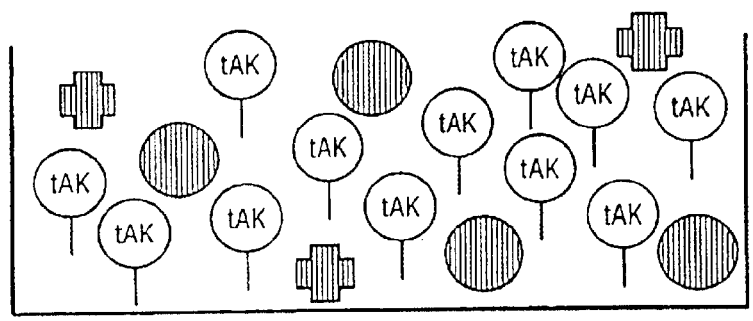
*10. ATP Bioluminescence*
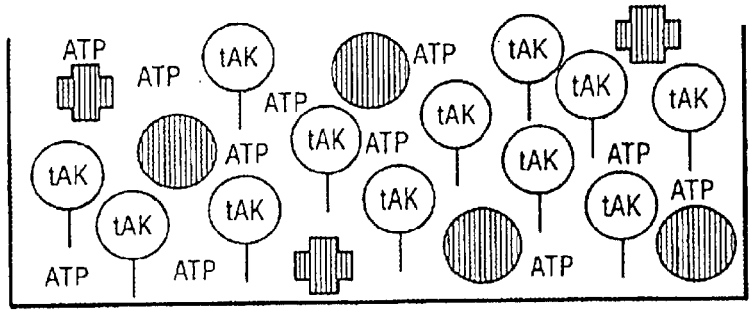
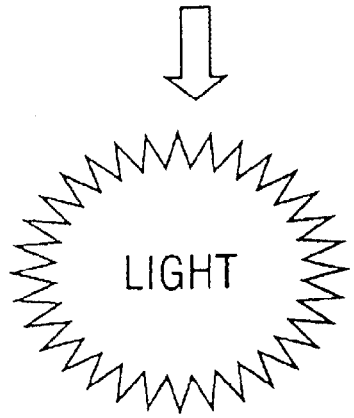

FIG. 4  Key to Prion ELISA
 - mesophilic adenylate kinase
 - prion protein
 - miscellaneous cellular materials
 - thermostable adenylate kinase
 - cleavable linker
 - antibody
 - antibody – thermostable adenylate kinase conjugate
ATP - adenosine 5'-triphosphate
 - apyrase / adenosine deaminase
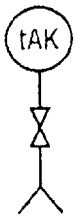 - thermally inactivated enzymes

SEQUENCE LISTING

```
<160> NUMBER OF SEQ ID NOS: 1

<210> SEQ ID NO 1
<211> LENGTH: 20
<212> TYPE: DNA
<213> ORGANISM: Artificial
<220> FEATURE:
<223> OTHER INFORMATION: synthetic oligonucleotide

<400> SEQUENCE: 1
catacacctc cagcacctaa                                    20
```

ASSAY WITH REDUCED BACKGROUND

This application is a 371 of PCT/GB00/00315 filed on Feb. 3, 2000 and published in English on Aug. 10, 2000.

FIELD OF THE INVENTION

The present invention relates to an assay with reduced background, a method of assaying for an analyte, a method of reducing background in an assay and apparatus, in particular a test kit, for carrying out such an assay.

RELATED ART

ATP bioluminescence has rapidly become the method of choice for hygiene and cleanliness monitoring due to its combination of sensitivity and ease of assay. A luciferin-luciferase bioluminescence assay can detect as little as $10^{-15}$ moles of ATP. Since an average microbial cell contains approximately $10^{-18}$ moles of ATP, this gives a detection limit of only $10^3$ cells.ml$^{-1}$.

For most operations this detection level is sufficient, however, there are applications where even greater sensitivity is required, even down to a single microbial cell. GB-A-2304892 describes such an assay using the ATP-forming enzyme adenylate kinase (AK). An average cell contains several hundred-fold less AK molecules than ATP molecules, however, in a 10 minute incubation, a typical 400,000-fold amplification is achieved by detecting AK through the ATP it produces. This corresponds to the level of single cell detection, although in practice 10 cells.ml$^{-1}$ is more readily achieved due to background AK and ATP contamination. It also corresponds to a detection level of down to at least $10^{-20}$ moles of AK.

The commercial use of this extreme sensitivity is, therefore, under investigation. There are, however, some problems with more widespread use of this known AK-based assay. One is that while the assay detects the presence of micro-organisms, it does not differentiate between one organism and another. This has been overcome to a degree by the use of bacteriophage to release AK from specific bacteria (Blasco R, Murphy M J, Sanders M F and Squirrell D J (1998) Specific assays for bacteria using phage mediated release of adenylate kinase. *J. Appl. Microbiol.* 84: 661∝666).

Each micro-organism, however, requires a specific phage and contains an AK with different buffer requirements, plus temperature and pH optima. The second problem is more fundamental and is a problem for its use as a generalised reporter enzyme. Whereas in hygiene and cleanliness monitoring the ubiquity of ATP and AK is beneficial, in an enzyme reporter assay any unwanted background activity is detrimental. This is especially so where the sample is greatly concentrated to maximise potential detection.

A further problem is that the known assay is only effective for microorganisms which contain AK; the known assay will not work with other biological material, such as viruses or other analytes, including other biological such material that does not contain AK.

Transmissible Spongiform Encephalopathies (TSEs) is the term given for a spectrum of diseases associated with an unconventional transmissible agent. The agent displays many virus-like features, such as strain variation and mutation, but differs from conventional viruses in being exceptionally resistant to heat, ultraviolet and ionising radiation and to chemical disinfectants. The TSEs are a heterogeneous group of fatal neurodegenerative disorders occurring in humans, mink, cats and ruminant herbivores. The endemic occurrence of the TSE "scrapie" in many sheep populations and more rarely human TSEs, such as Creutzfeldt-Jakob Disease (CJD), has been known for some time. The occurrence of novel TSEs in wild populations of mule deer and elk in the United States and an outbreak of "Bovine Spongiform Encephalopathy" (BSE)" in cattle in the United Kingdom and Europe has, however, emphasised the need for sensitive and reliable diagnostic tests and detection systems for these diseases. More recently, however, it has become apparent that BSE has crossed the species barrier to the human population giving rise to a new variant TSE, generally known as "new variant CJD" (nvCJD) or "variant CJD" (vCJD).

The highest native concentrations of TSE infectivity are found in 263K infected hamster brain where titres as high as $10^{10}$ infectious units per gram of tissue are frequently reported.

Current immunoassays give positive signals for PrP$^{Sc}$ from as little as 1–10 g of TSE infectious brain tissue, e.g. by Western blotting or ELISA. ELISA, however, is considerably more suitable than Western blotting for the development of a fast and practical PrP (PrP$^c$+Prp$^{Sc}$) detection system. This level of detection is approximately $10^{-14}$ moles of Prp$^{Sc}$ but insufficient to detect the presence of still infectious quantities of PrP$^{Sc}$. Where PrP$^c$ is also included, however, the differential between the current and required level of sensitivity is significantly reduced. This brings current immunoassays potentially into the appropriate range, but with an inadequate margin of safety.

There is currently great uncertainty regarding the numbers of individuals in the UK potentially or actually infected with new variant Creutzfeld-Jakob Disease (nvCJD). As a result there have been calls that all surgical procedures should be carried out using disposable instruments as a safeguard. Implementation has severe cost and procedural implications, consequently an alternative means to validate decontamination would be extremely beneficial, and would also be of benefit to other equipment such as meat processing equipment. Therefore, it remains a problem to provide an alternative assay for biological material, especially prior protein, preferably of increased sensitivity.

WO 94/06933 discloses the use of a conjugate comprising a pyruvate kinase linked to an antibody in an assay for biological compounds and a process for the production of the enzyme-antibody conjugate.

Antibody-enzyme conjugates in which the enzyme may be thermostable have been disclosed in EP 0 304 934.

U.S. Pat. No. 4,584,272 describes an adenylate kinase that retains at least 80% of its activity when incubated at 50° C. for 15 minutes.

The use of antibodies to detect prion proteins is known from, for example, WO 97/10505. No assay is specified for the use of these antibodies.

SUMMARY OF THE INVENTION

The present invention is aimed at addressing and overcoming or at least ameliorating these problems. A further object of specific embodiments of the present invention is to develop a rapid and sensitive method for assay of biological material, in particular for the detection of prion protein PrP (PrP$^c$ and PrP$^{Sc}$)—as the presence of either isoform in a sample is indicative of the presence of residual PrP-expressing tissue and the potential for transmissible infectivity. A still further object of specific embodiments of the present invention is to provide a method for assay of prion proteins that may be used in the screening of cleaning protocols to determine their suitability for the removal of TSE agents from surfaces and delivery of recovered material for immunoassay.

Accordingly, a first aspect of the invention provides an assay for an analyte, comprising specifically associating the analyte with a reporter kinase, adding ADP and testing for formation of ATP wherein, prior to addition of ADP, kinase other than reporter kinase is substantially removed.

BRIEF DESCRIPTION OF THE FIGURES

FIG. 1 is a graphical representation depicting steps 1–4 as set forth in Example 1.

FIG. 2 is a graphical representation depicting steps 5–8 as set forth in Example 1.

FIG. 3 is a graphical representation depicting steps 9 and 10 as set forth in Example 1.

FIG. 4 provides definitions for the symbols depicted in FIGS. 1–3.

DETAILED DESCRIPTION OF THE INVENTION

Thus, in use of an assay of the present invention, a reporter adenylate kinase is specifically associated with the analyte so that the amount of reporter adenylate kinase is substantially in proportion to the amount of analyte present. In the absence of analyte there will be no reporter adenylate kinase associated and no signal generated. By substantially removing adenylate kinase other than reporter adenylate kinase, the present invention has the advantage that the signal obtained is not contaminated or otherwise adversely affected by any endogenous adenylate kinase that might have been present in a sample being tested. By reference to removing adenylate kinase it is intended to refer to removing adenylate kinase activity, such as by removing the adenylate kinase, or denaturing or otherwise inactivating it in situ. Furthermore, by addition of reporter adenylate kinase, the assay is of application for detection of substantially any analyte and, unlike the prior art, is not limited to detecting analytes that comprise their own adenylate kinase.

In an embodiment of the invention there is provided a method of determining presence and/or amount of an analyte in a sample, comprising:— exposing the sample to a reporter adenylate kinase coupled to a binding agent specific for the analyte, so that the reporter adenylate kinase is specifically associated with any analyte present in the sample;

removing reporter adenylate kinase that is not specifically associated with analyte;

exposing reporter adenylate kinase specifically associated with the analyte to ADP; and testing for formation of ATP;

wherein prior to addition of ADP adenylate kinase other than reporter adenylate kinase is substantially removed.

Typically, the reporter adenylate kinase is coupled to an antibody that binds specifically to the analyte under investigation. The antibody may be obtained using conventional techniques for identification end isolation of specific antibodies, and the assay of the present invention is thus of application to substantially all analytes against which an antibody can be raised. This confers the advantage that the present invention is of considerably wider application compared to the known AK/ATP-based assays, as the previous assays were restricted to target analytes that contained their own adenylate kinase.

The reporter adenylate kinase is suitably coupled to the specific binding agent by conventional techniques. For example, there are numerous ways of labelling immunoreactive biomolecules with enzymes (conjugation). Antibodies, the majority of antigens, and enzymes are all proteins and, therefore, general methods of protein covalent cross-linking can be adapted to the production of immunoassay reagents. The preparation of antibody-enzyme conjugates requires mild conditions to ensure the retention of both the immunological properties of th antibody and the catalytic properties of the enzyme. Common methods include, glutarald hyde coupling, the use of periodate oxidation of glycoproteins to generate dialdehydes capable of forming Schiff-base linkages with free amino groups on other protein molecules, and the use of heterobifunctional reagents, for example, succinimidyl-4-(N-maleimidomethyl)cyclohexane-1-carboxylate (SMCC).

Endogenous adenylate kinase present in the analyte is substantially removed or destroyed or otherwise inactivated before testing for formation of ATP is carried out. This removal step can conveniently be achieved by heating the endogenous adenylate kinase to a temperature at which it is denatured. Alternatively, other treatments might be appropriate to destroy the activity of the endogenous adenylate kinase, such as the use of ultrasound or extremes of pH or salt concentration. In an embodiment of the invention, the reporter adenylate kinase is a thermostable enzyme and endogenous adenylate kinase is removed by heating. In a specific embodiment of the invention described in more detail below, this denaturing step is carried out at about 90° C. for a period of about 10 minutes, though other temperatures and durations will be appropriate so long as the endogenous adenylate kinase is rendered incapable of catalysing the formation of ATP and the reporter adenylate kinase retains its activity.

It is a further, preferred, step in the assay of the present invention for any ATP present prior to addition of ADP to be removed, thereby further decreasing the background noise in the assay. The removal of endogenous ATP may be achieved by addition of an ATPase and incubation prior to adding ADP. More preferably, a thermolabile ATPase is used to remove ATP and then the thermolabile ATPase is itself destroyed by use of elevated temperature, to avoid the presence of the ATPase adversely influencing the signal obtained using the thermostable, reporter adenylate kinase.

The precise order of carrying out the steps of the present invention is not critical, provided that endogenous adenylate kinase is destroyed before addition of ADP and testing for the formation of ATP. Thus, the method of the present invention can be carried out by treating a sample to destroy its endogenous adenylate kinase, adding reporting adenylate kinase coupled to an antibody specific to the analyte, isolating reporting adenylate kinase that is specifically associated with analyte and then adding ADP and testing for formation of ATP. Alternatively, the assay can be carried out by adding a reporter adenylate kinase coupled to an antibody specific for the analyte to a sample, isolating reporter adenylate kinase that is specifically associated with analyte, destroying any endogenous adenylate kinase that may be present and then adding ADP and testing for formation of ATP. A further alternative is to add reporter adenylate kinase coupled to an antibody specific for analyte to the sample, treating the sample to destroy endogenous adenylate kinase, isolating reporter adenylate kinase specifically associated with analyte and then adding ADP and testing for formation of ATP.

In a specific embodiment of the invention described in more detail below, an assay is carried out by following the steps:—

1. An antibody specific to the analyte is immobilised on a solid phase.
2. A sample is combined with the solid phase so that analyte present in the sample can bind to the antibody.
3. The solid phase is washed, thereby washing away components of the sample and retaining on the solid phase only any analyte that has bound to the immobilised antibody.
4. A reporter composition is added to the solid phase, the reporter composition comprising an antibody which is specific to the analyte and which is coupled to a thermostable adenylate kinase.
5. The solid phase is washed, thereby washing away unbound components of the reporter composition and retaining reporter composition that has specifically bound the analyte, the analyte being itself bound to the immobilised antibody.
6. The solid phase is heated to denature any endogenous adenylate kinase that may be present but so as not to denature the thermostable adenylate kinase.
7. Optionally, a thermolabile ATPase is added to the solid phase to remove any endogenous ATP.
8. Optionally, the solid phase is heated to destroy the thermolabile ATPase of step 7.
9. ADP is added to the solid phase which is then tested for presence and/or amount of ATP.
10. If ATP is detected, this indicates that adenylate kinase in the reporter composition was bound to the solid phase, ie that analyte was present in the sample.

The solid phase is suitably selected from conventional solid phases used in immunoassays, and can for example be a microtitre well, a column, a dip-stick or a bead, such as a latex or a magnetic bead. Examples of further suitable solid supports are nitrocellulose, polyvinylchloride, polystyrene, diazotized paper, activated beads having a range of appropriate linking agents and S.aureus protein A beads. More thermostable supports are provided by plastics such as polypropylene, polycarbonate, polyphenylenine oxide polymethylpentene and fluoropolymers (e.g. PTFE, PFA, FEP and EFTE). The solid support can have several forms dependent upon the type of support and the conditions required. Commonly these will be microtitre plates, where each individual well serves as an independent incubation chamber. Similarly, membranes or sheets can be used providing lateral diffusion is limited. Alternatively, beads can be used, which enable the separate reactions to be performed in different tubes under different conditions. These individual matrix materials can be purchased in a variety of forms, as appropriate for the particular type of assay.

Firefly luciferin catalyses the oxidation of D(−) luciferin in the presence of ATP-Mg$^{2+}$ and $O_2$ to generate oxyluciferin and light. The quantum yield for this reaction (0.88) is the highest known for bioluminescent reactions (Gould and Subramini, 1988). Firefly luciferase, however, is relatively unstable and has, therefore, not proved readily adaptable as an immunoassay label (Kricka, 1993). By contrast, in the present invention, the luciferase enzyme can be operated under its optimal conditions and is not exposed to harsh treatments such as antibody-coupling.

A number of extremely thermostable adenylate kinases have now been characterised (Ki and Takahisa, 1988; Lacher and Schäfer 1993; Rusnak et al., 1995) and are suitable for use in the present invention. One has been cloned and overexpressed in E. coli (Bonisch et al., 1996) and the full sequences of a range of others are now available as a result of genome sequencing programmes. A rapid and simple purification scheme is thus available to produce homogenous adenylate kinase. Initially a thermal denaturation step can be employed to denature the bulk of E. coli proteins (~90–95%) while retaining the thermostable activity in solution.

This procedure has been successfully employed in embodiments of the present invention with several recombinant thermostable enzymes. Subsequently a generally applicable affinity purification procedure can be utilised to yield th purified enzyme. This involves binding of the enzyme to a mimetic dye matrix and selective desorption with the adenylate kinase inhibitor $P^1$, $P^5$-di(adenosin-5') pentaphosphate (Rusnak et al., 1995). The use of stable enzymes overcomes problems associated with inactivation upon antibody-coupling, and also provide other benefits. Since the activity is extremely thermostable, once substrate binding and removal of unbound components has occurred, the temperature can be increased to e.g. 70–90° C., denaturing and inactivating any residual contaminating mesophilic adenylate kinase. Additionally, on cooling, a mesophilic ATPase (or apyras can be added to remove any residual ATP. This ensures that no ATP or AK background is now present. A further heat incubation inactivates the mesophilic ATPase and ADP is added in order to generate ATP derived exclusively from the thermostable adenylate kinase. This ATP is then available for conventional luciferin-luciferase bioluminescence detection. A potentially contaminating ATP signal is now only possible from three sources: non-specifically bound thermostable AK, ATP-contaminated ADP and AK contaminated luciferase. The latter two can be eliminated by the use of high purity reagents and careful handling. In each case, however, contamination would result in a positive signal, i.e. a PrP-free sample might be determined to be PrP-containing but the opposite could not occur.

A known thermostable adenylate kinases, *Methanococcus jannaschii* has a very high specific activity, namely 89 $\mu$mol of ATP mg$^{-1}$ min$^{-1}$. This corresponds to a turnover number in excess of 2000 min$^{-1}$ and the potential to produce more than $1.2 \times 10^5$ molecules of ATP per molecule of AK in an hour's incubation. Since $6 \times 10^8$ molecules of ATP are detectable by ATP-bioluminescence then as few as $5 \times 10^3$ molecules of PrP would be detectable. This is 40-fold lower than the minimum number of PrP$^{Sc}$ molecules identified as constituting a single infectious unit. An additional safety margin is provided by the presence of much higher quantities of PrP$^c$ in relation to PrP$^{Sc}$ indicating that the present invention exceeds the required sensitivity by several orders of magnitude.

As an alternative to use of an analyte-specific antibody to immobilize analyte on the solid phase, the solid phase may be provided with analyte immobilised directly thereon without the presence of the first antibody. For example, the solid phase can itself be a substrate potentially contaminated by an amount, typically a trace amount, of analyte. This is the case in respect of medical equipment potentially contaminated by very small amounts of prion protein which are effectively immobilised on the surface of the equipment. The assay is of use in testing for the presence of the analyte for example following cleaning of the equipment. Analyte can also be immobilised non-specifically.

The method of the present invention may be carried out utilising relatively inexpensive equipment in a standard laboratory. Use of a method of the present invention to determine when the level of prion protein has been reduced to below detectable and, by extrapolation, infectious levels may be used to confirm the decontamination of instruments, equipment and other items potentially exposed to TSE infectious agents, permitting their safe use.

In use of a specific embodiment of the invention, the first washing step can be repeated a number of times, in accordance with conventional practice in this field, the object being to remove from the solid phase all components of the sample that have not bound specifically to the immobilised antibody. Thus, if there is no analyte present in the sample then the washing step will remove the whole of the sample and ultimately the assay will give no signal, indicating that no analyte was present. The antibody in the reporter composition binds to the same analyte as the antibody immobilised on the solid phase. The antibody and the reporter composition can in fact have the same binding properties as the immobilised antibody, though it is an alternative for the reporter antibody to bind to a different site on the same analyte. The reporter antibody is preferably selected so that the amount of reporter composition that binds to the analyte is substantially proportional to the amount of analyte present. The second washing step can, in line with the first, be repeated a number of times in accordance with conventional practice, the object of the second washing step being to remove all components of the reporter composition that have not specifically bound to analyte which itself has specifically bound to immobilised antibody. Thus, if no analyte is present on the solid phase the second washing step is to remove all reporter composition, leading ultimately to no signal being generated in the assay, indicating no analyte was present in the sample under investigation.

This latter embodiment represents use of the principles of the invention in a two antibody capture assay, sometimes referred to as a sandwich assay. The invention is similarly of application in antigen capture assays and antibody capture assays.

Thus in a further embodiment of the invention, an assay for analyte comprises specifically associating an analyte with a reporter adenylate kinase, wherein the analyte is bound to a solid phase. This embodiment may be referred to as being of the antibody capture type. Binding of the analyte to the solid phase can be achieved by non-specifically binding the analyte to the solid phase and then treating the solid phase to prevent further non-specific binding thereto— in this way, a number of components from a sample are bound to the solid phase, which components include the analyte of interest if present in the sample, and subsequent treatment ensures that when an antibody is added to detect the analyte that antibody will only bind to the solid phase if analyte is present.

The use of heat to denature any endogenous kinase that may be present has been carried out in an embodiment above as step 6, though as mentioned this step can be carried out at an alternative juncture in the assay provided that it is carried out before addition of ADP. Further, ADP may be added before the ATPase provided the ATPase has no ADPase activity. The temperature and duration adopted are chosen so as to be sufficient to denature th endogenous adenylate kinase whilst leaving intact the reporter adenylate kinase, this reporter adenylate kinase preferably being a thermostable enzyme. In a specific embodiment described below, heating to a temperature of about 90° C. for about 10 minutes has been found effective. Sufficiently thermostable adenylate kinases may be found amongst a range of bacterial and archaeal genera and families. In the Bacteria, they may be produced, for example, by members of the genera *Alicyclobacillus, Ammonifex, Aquifex, Bacillus, Caldariella, Calderobacterium, Caldicellulosiruptor, Caldocellum, Caloramator, Carboxydothermus, Chloroflexus, Clostridium, Coprothermobacter, Dictyloglomus, Fervidobacterium, Geotoga, Hydrogenobacter, Hydrogenothermophilus, Meiothermus, Petrotoga, Rhodothermus, Rubrobacter, Thermoactinomyces, Thermoanaerobacter, Thermoanaerobacterium, Thermoanaerobium, Thermobacterium, Thermobacteroides, Thermobifida, Thermobispora, Thermobrachium, Thermochromatium, Thermocrispum, Thermodesulfobacterium, Thermodesulforhabdus, Thermodesulfovibrio, Thermohydrogenium, Thermomicrobium, Thermomonospora, Thermonema, Thermonospora, Thermopolyspora, Thermosipho, Thermosphaera, Thermosyntropha, Thermoterrabacterium, Thermotoga* and *Thermus*. Amongst the archaea, they may be produced, for example, by members of the genera *Acidianus, Aeropyrum, Archaeoglobus, Desulfurococcus, Desulfurolobus, Ferroglobus, Hyperthermus, Metallosphaera, Methanobacterium, Methanococcus, Methanopyrus, Methanothermus, Picrophilus, Pyrobaculum, Pyrococcus, Pyrodictium, Pyrolobus, Staphylothermus, Stetteria, Stygiolobus, Sulfolobus, Sulfophobococcus, Thermococcus, Thermofilum, Thermoplasma* and *Thermoproteus*.

It is preferred, though optional, also to carry out a step of removing endogenous ATP from the sample using a thermolabile ATPase and subsequently destroying this latter enzyme, again conveniently using heat. In a specific embodiment of the invention described below, an incubation of about 10 minutes has been effective using a thermolabile ATPase and this enzyme has been then denatured by temperatures of about 90° C. for 5 minutes. ATP can be released from cells or other cellular components after heating. Therefore, it is preferred that the step of removing ATP is carried out after an initial heating of the sample, for example after the step of using heat to destroy endogenous adenylate kinase.

It is further preferred to use ultrapure ADP, free of ATP, to avoid risk of background from contaminating ATP. As an alternative to the use of a pre-purified ultrapure form of ADP, ATP-free ADP can be generated in situ by the addition of an essentially irreversible and strictly ATP-dependent mesophilic kinase plus its substrate, for example, yeast hexokinase and glucose. ATP present is converted to ADP and the kinase is inactivated by heat prior to the incubation with thermostable adenylate kinase. Similarly, it is also preferred to use other reagents form of contamination by kinase or ATP. Luciferin and luciferase can contain adenylate kinase contamination and so it is preferred to use purified forms of these, or recombinant forms of luciferase. Luciferin is preferably the d-isomer as the l-isomer can inhibition the luminescence reaction.

The invention is of particular application to detection of diseases such as vCJD, which by December 1999 had resulted in approximately 50 deaths in the UK, with further cases reported in France and Ireland. Due to the long and variable incubation period for this new disease however, there is currently great uncertainty regarding the total numbers of individuals in the UK potentially or actually infected with vCJD. Affected individuals will frequently present with symptoms requiring neurological examination or may merely undergo common surgical procedures such as tonsillectomy or appendectomy along with the general population. A wide range of tissues, including tonsil and appendix, has been shown to harbour vCJD infectivity in addition to brain and spinal cord. This gives rise to a significant potential for transmission of infection by exposure to contaminated surgical instruments, since complete elimination of infectivity is not achievable using conventional sterilisation procedures.

Although the nature of the responsible agent is not fully understood, infectivity appears to be associated very closely with the abnormal conformation ($PrP^{Sc}$) of a normal central nervous system protein ($PrP^c$), designated the "prion" protein. Although the prion is not universally accepted as being solely responsible for infectivity, there is general agreement that it has an intimate association with it. Detection of prion protein is, therefore, considered to be an excellent measure of the potential presence of TSE infectivity. Prions have a tendency to form insoluble aggregates and are highly hydrophobic. There is, therefore, considerable doubt as to whether they can be reliably detached from surfaces and solubilised for detection by conventional enzyme-linked immunosorbent assay. This is particularly important for items like surgical instruments, where the presence of a very small amount of residual material after attempted decontamination, could give rise to iatrogenic transmission of vCJD infection. In a specific embodiment, the invention describes an assay which permits in situ detection of the prion protein (Prion ELISA 1–3).

Since the presence of any residue containing either $PrP^c$ or $PrP^{Sc}$ indicates that the test item is not completely clean, the antibody selected need not discriminate between the different conformers. This greatly increases the range of antibodies available. The $PrP^{Sc}$ conformation is, however, considerably more persistent and in general it is the form associated with infectivity which will be detected.

Thyroid stimulating hormone (TSH) is secreted by the anterior pituitary of the brain. This hormone acts upon the thyroid, stimulating the production of the hormones T3 and T4. The level of TSH is controlled by a negative feed-back system that maintains a constant level of free TSH. Hyperthyroidism is a condition caused by reduced levels of circulating TSH.

Diagnostic assays for the diagnosis of hyperthyroidism must be able to distinguish between hyperthyroidism and normal levels of circulating hormone. The assays should be able to monitor a very low signal without interference. In addition, assays for the measurement of circulating TSH should have a broad dynamic range. A specific embodiment of the invention, described below in more detail, provides an assay for a blood hormone.

Assays for drugs of abuse are routinely used by clinical laboratories, drug rehabilitation clinics, health officials and clinical justice facilities. The data obtained is often used to support medical-legal applications involving custody of children. A decision to renew custody of a child often rests on the results of urine drug analyses demonstrating prolonged abstinence of drug abuse, by the parent. In many countries random urine testing is mandatory in sensitive government posts, the armed forces and the transport industries. There is a requirement for more sensitive and rapid assays for drugs of abuse.

The principal agent produced by *Cannabis sative* is δ-9-tetrahdrocannabinol (THC). Only a small amount of THC is excreted in the urine and the majority of assays are designed to detect the main inactive oxidation product, 11-nor-δ-tetrahydrocannabinol-9-carboxylic acid (11-COOH-THC). A specific embodiment of the invention, described in more detail below, provides an assay for cannabis metabolite.

Urine is a complex medium, which exacerbates the problem of distinguishing a signal from that of background instrument noise. This is overcome in commercial assays by assigning a threshold concentration, above which a sample is considered positive, that exceeds the detection limit by several orders of magnitude. In practice this results in a number of positive samples being assigned as negative as their signals are below the assigned threshold. More sensitive assays make it easier to discriminate between positive and negative samples.

Many of the current commercial assays involve enzyme multiplied immunoassay (Emit). This ELISA involves competition between drug in the test sample and drug labelled with glucose-6-phosphate dehydrogenase (G6PDH). The G6PH drug conjugate is inactive when immobilised to a solid-phase comprising of an antibody specific for the drug of interest. On displacement the free drug-G6PH conjugate is detected by a change in the optical density at 340 nm, as NAD+ is reduced to NADH and the substrate is glucose-6-phosphate is oxidised. A further specific embodiment of the invention provides an assay for cocaine metabolites in urine.

It is known that human papilloma virus (HPV) infection is a prerequisite of the oncogenesis of many forms of cervical cancer. Currently cervical smears are screened for the presence of viral infection as a predictive precursor of oncogenesis. Another specific embodiment of the invention is a rapid screen for the presence of viral infection of cervical cells.

Combinational libraries are powerful tools for drug discovery. The sensitivity of the screening methodology is a major limit on the number of combinations that can be screened for in a combinational library. A library comprised of every combination of an hexa-peptide is composed of $20^6$ possible combinations. More sensitive assays for the detection of target sequences would allow more extensive libraries to be screened. In a yet further specific embodiment of the invention a thermostable AK is used to screen a combinational peptide library for a sequence that binds a specific ligand of interest. This ligand may be a receptor or an enzyme.

Botulinum toxins are produced by the bacterial species *Clostridium botulinum* and are the causative agents of food-borne botulism. The most sensitive accepted method for the detection of botulinum toxins is the mouse lethality test. Few ELISA based assays using conventional amplification methodology have the sensitivity required. A yet further embodiment of the invention describes an ELISA based assay for the detection of botulinum neurotoxin in foods.

The present invention also provides, in a second aspect, apparatus for determining the presence and/or amount of analyte in a sample, comprising:—

- a solid phase on which is immobilised the analyte or an antibody specific for the analyte;
- a reporter composition comprising a thermostable kinase coupled to an antibody specific for the analyte; and
- ADP plus, optionally, associated reagents for conversion of ADP into ATP by thermostable kinase.

An optional additional component of the apparatus is a thermolabile ATPase.

The components of the apparatus may be combined into a test kit for determining presence and/or amount of an analyte in a sample.

Testing for formation of ATP may be carried out using a number of conventional means, including formation of colour. Particularly preferred is the use of luciferin/luciferase reagents in combination with calibration curves to determine both presence and amount of analyte. The presence of magnesium ions is usually required for formation of ATP, and further details are provided in the prior art publication GB-A-2304892, the contents of which are incorporated herein by reference.

The present invention has been described in relation to the use of kinases, in particular thermostable adenylate kinase.

More generally, the invention also provides, in a third aspect, an assay for determining presence and/or amount of an analyte in a sample, comprising:— exposing the sample to a detector composition, the detector composition comprising an antibody specific to the analyte coupled to a thermostable enzyme;

isolating (i) detector composition that has specifically bound to analyte from (ii) detector composition that has not specifically bound to analyte;

determining the presence and/or amount of detector composition that has bound to analyte by adding a substrate for the thermostable enzyme;

wherein prior to adding the substrate non-thermostable enzymes are destroyed by application of heat.

The thermostable enzyme is suitably a kinase, and may be selected from pyruvate kinase, adenylate kinase and acetyl kinase. All of these catalyse formation of ATP from ADP and may be used with reagent such as luciferin/luciferase.

It is preferred that prior to addition of the substrate background product is removed, which assists in reducing or limiting background in the assay. Background product is suitably removed by the action of enzyme or by thermal inactivation.

The third aspect of the invention also provides apparatus for determining presence and/or amount of analyte in a sample, comprising:— a solid phase on which is immobilised the analyte or an antibody specific for the analyte;

a reporter composition comprising a thermostable enzyme coupled to an antibody specific for the analyte; and substrate for the thermostable enzyme.

This aspect of the invention confers the advantage that the signal obtained from the thermostable enzyme is substantially not contaminated by any background signals or background noise that may otherwise be obtained from the action of non-thermostable enzymes on the substrate.

Background signals and/or background noise are thus reduced and possibly even removed entirely. In use of a method of the third aspect of the present invention, an analyte is immobilised on a solid phase, a sample is combined with the solid phase and then the solid phase is washed, the solid phase is exposed to a detector composition including an antibody specific to the analyte coupled to a thermostable enzyme, the solid phase is then again washed, the solid phase is then heated to denature non-thermostable enzymes but so as not to denature the thermostable enzyme of the detector composition, and the amount of thermostable enzyme specifically bound to analyte which itself is specifically bound to the solid phase is determined by adding a substrate for the thermostable enzyme and determining how much product is then obtained. Immobilisation of the analyte can be through use of an analyte-specific antibody immobilised on the solid phase, or by directly binding the analyte to the solid phase.

A further aspect of the invention provides a conjugate comprising an antibody conjugated to a thermostable enzyme for use in the assay of any preceding aspect of the invention. In an embodiment of the invention, the enzyme an adenylate kinase. The antibody may suitably bind to an analyte selected from a protein, a microorganism, a peptide, a toxin, a hormone and a metabolite. In a specific embodiment, the antibody binds to a prion protein.

A stil further aspect of the invention lies in use of the apparatus of the invention or the conjugate of the invention in an assay for an analyte.

The present invention is thus suitably employed to investigate the effectiveness of a range of agents with potential for surface cleaning of contaminated surfaces to remove cellular material and PrP. Steel, glass and plastic surfaces can all be investigated to determine whether any one is particularly recalcitrant to cleaning, and PTFE can be used as a control surface for comparative purposes.

Thermostable adenylate kinases may be purified from a number of thermophilic and hyperthermophilic microorganisms using a combination of ion exchange, gel filtration and affinity chromatography. The adenylate kinases may be cloned and expressed in *E.coli* in plasmid or phage libraries. Direct expression can be screened for (after replica plating) by examining pooled colonies for thermostable adenylate kinase activity by incubation with ADP, followed by ATP bioluminescence assay.

A range of commercially available coupling reagents is available for antibody-adenylate kinase conjugation. Both the antibody and the adenylate kinase can be re-purified by affinity chromatography.

In certain uses of the invention, such as in the case that there is no endogenous adenylate kinase or no microbial contamination of the sample or if the risk of such contamination is removed, it is optional to dispense with the step of removing endogenous adenylate kinase. The method of the invention then comprises specifically associating the analyte with a reporter adenylate kinase, adding ADP and testing for formation of ATP. Preferably, prior to addition of ADP, ATP is substantially removed, for example by the use of an ATPase.

Specific embodiments of the invention are now described.

The assay of the present invention can involve the use of conventional equipment and reagents required for known ATP/AK bioluminescence assays, supplemented by a thermal cycler (widely and inexpensively available for PCR), plus two specific enzymes, a thermolabile ATPase and a thermostable adenylate kinase.

EXAMPLES

Example 1

Assay for Prior Protein

Prion ELISA—1

(Reference is Made to the Attached Drawings)

1. Blocking

A standard item of potentially infectious equipment presents with a diverse range of biological material bound to the surface. This includes both free and cellular ATP and mesophilic adenylate kinases (mAK). A small area of the surface is sectioned off to form a chamber (not shown, ~1 ml volume) into which reagents can be added and removed. To prevent non-specific binding of the antibody-thermostable adenylate kinase conjugate, the exposed surfaces, including the enclosed area of the surgical instrument, are "blocked" by incubation in the presence of buffer containing, for example, the non-ionic detergent Tween 20 (1% v/v) in 10 mM PBS pH7 for 1 hour. The chamber is then washed twice with 0.05% Tween 20 in 10 mM PBS pH7 prior to binding of the antibody-thermostable adenylate kinase conjugate.

2. Antibody Binding

The thermostable adenylate kinase from *Bacillus stearothermophilus* is coupled to an affinity-purified polyclonal antibody via a heterobifunctional thiol-cleavable cross-linking agent, N-Succinimidyl-3-(2-Pyridyldithio) Propionate (SPDP). The antibody is raised by standard procedures against a synthetic peptide corresponding to a conserved region of the prion protein, coupled to maleimide-activated keyhole limpet haemocyanin. Active conjugate (50 µl) is added to the buffer in the chamber and incubated for 30 minutes at room temperature.

3. Washing

The chamber is washed manually or by use of an automated washing device with six changes of buffer containing 0.2 M NaCl, 0.05% Tween 20 in 10 mM PBS, pH7. These serve to remove unbound conjugate and any biological material only loosely attached to the surface.

4. Linker Cleavage

Dithiothreitol is added to the last wash to a final concentration of 25 mM and incubation at room temperature continued for 30 minutes. This cleaves the thermostable adenylate kinase moiety from the bound antibody providing a signal molecule in free solution proportional to the original amount of prion protein present.

Prion ELISA 2

5. Recovery/Transfer

At this stage the thermostable adenylate kinase-containing solution is aspirated by pipette and transferred to the wells of a thermostable luminometer microtitre plate. Transfer of non-specific background ATP and mesophilic adenylate kinase also occurs, giving the potential for overestimation of prion protein present on the original instrument surface.

6. Thermal Inactivation

The adenylate kinase used is thermostable. The temperature is, therefore, increased to 80° C. and maintained at this temperature for 10 minutes in a microtitre plate thermal cycler. This thermally denatures and inactivates any residual contaminating mesophilic adenylate kinase leaving a preparation containing only the specific thermostable adenylate kinase proportional to the prion protein content of the sample.

7. ATP Hydrolysis

The plate is then cooled and 0.05 units.ml$^{-1}$ of adenosine deaminase and *Solanum tuberosum* apyrase added prior to incubation at 30° C. for 30 minutes. This enzyme removes any residual ATP carried over from the original sample.

8. Thermal Inactivation

The combination of steps 6 & 7 ensures that no ATP or AK background is now present. A further heat incubation as in step 6 is then used to inactivate the mesophilic apyrase.

Prion ELISA —3

9. ATP Generation

Ultrapure ADP (0.1 mM) and free of ATP, is added along with magnesium ions (10 mM) in order to generate ATP derived exclusively from the thermostable adenylate kinase. Incubation is carried out at 80° C. for 30 minutes. The ATP is then available for D-luciferin-luciferase bioluminescence detection.

10. ATP Bioluminescence

The ATP-containing wells are cooled to 25° C. and synthetic ultrapure D-luciferin and adenylate kinase-free luciferase added to a concentration of 40 $\mu$M and 1 mg.l$^{-1}$ respectively. Individual wells are read for ATP-d pendent bioluminescence in a microtitre plate luminometer and the results recorded. The amount of light generated correlates directly with the original amount of prion protein in the sample.

Example 2

An Assay for a Microorganism

A micro-organism is immobilized onto solid surface by non-specifically binding sample components including the microorganism to the solid phase, treating the solid phase to prevent further non-specific binding thereto and washing (we use a microtitre well in this case but other known solid phases are suitable, such as a latex bead or a magnetic bead). An antibody specific to the micro-organism and coupled to a thermostable adenylate kinase is introduced and allowed to bind, prior to further washing/recovery.

(In the known AK assay, sensitivity would have been limited by the level of sample concentration possible before levels of background ATP and non-specific AK obscured any signal).

The sample is now heated to about 90° C. for about 10 minutes in a cell extraction buffer (in a thermal cycler) to denature any endogenous AK present and release any ATP that may be trapped within the micro-organism. The sample is then cooled to 37° C. and a thermolabile ATPase added. The sample is incubated for about 10 minutes to remove the background ATP, then the temperatures is raised to about 90° C. to denature the thermolabile ATPase.

Next, ADP is added and the temperature maintained at 90° C. so the thermostable adenylate kinase can convert ADP into ATP. This incubation generates ATP exclusively from the thermostable adenylate kinase. The ATP thus generated is then assayed by conventional ATP bioluminescence and is directly proportional to th concentration of the target present.

Example 3

An Assay for a Microorganism

A micro-organism is captured by a conventional capture technique, using a specific antibody immobilised onto a solid surface (we use a microtitre well in this case but other known solid phases are suitable, such as a latex bead or a magnetic bead). After washing/recovery, a second antibody specific to the micro-organism and coupled to a thermostable adenylate kinase is introduced and allowed to bind, prior to further washing/recovery.

Thus, the method of Example 1 is repeated but using a microorganism immobilized using antibody.

Example 4

A Blood-Hormone Assay

An antibody specific for the alpha subunit of TSH is immobilised onto a solid-phase. The solid-phase is treated to prevent further non-specific binding thereto. The solid-phase is washed with wash buffer, optionally containing detergent. A test sample of blood serum is added.

The sample is then incubated, e.g.: 37° C. for 60 mins, allowing the free TSH in the sample to bind to the capture antibody. The solid-phase is then washed to remove non-specifically bound material and an antibody specific for the beta subunit of TSH is added, to which a thermostable adenylate kinase reporter enzyme has been conjugated. The conjugate is then incubated at 37° C. for 60 minutes, or equivalent.

Non-bound material is then removed by washing and any endogenous ATP present on the solid-phase is removed by the addition of adenosine-5'-triphosphatase (an alternative is apyrase). The sample is then heated to 90 C, or equivalent, to denature and inactivate any mesophilic adenylate kinase that may be present.

Adenosine diphosphate (ADP) is added and the temperature is maintained at 90 C so that the thermostable adenylate kinase can convert the ADP to ATP. This incubation generates ATP exclusively from thermostable adenylate kinase. The ATP generated is then assayed by conventional ATP bioluminescence technology using a luciferin/luciferase reaction. Signal from contaminating adenylate kinase in the luciferin/luciferase reagents may be quenched by the addition of a specific enzyme inhibitor. The ATP bioluminescence measured is directly proportional to the concentration of the TSH in the original test sample.

Whilst the solid-phase used in the above is a microtitreplate, other solid-phases are suitable, such as latex or magnetic bead. The test sample may be whole blood or other body fluid, rather than blood, and the antibody may be a polyclonal or a monoclonal antibody.

Example 5

An Assay for Cocaine Metabolites in Urine

A thermostable G6PDH is used as reporter enzyme. Test antibody specific for the class of drug of interest is immobilised onto a micro-titre plate as solid-phase. The solid-phase is treated to prevent further non-specific binding thereto. The solid-phase is washed with wash buffer, which may or may not contain detergent. A test sample of urine is added along with the drug-G6PDH conjugate. The drug-G6PDH is thermostable and is not active when bound to the antibody immobilised to the solid-phase.

The sample is then incubated, at 37° C. for 60 mins. The contents of the micro-titre well is then removed and heated to 90° C. to inactivate any mesophilic G6PDH present. The temperature is then maintained at 90° C. and the substrate glucose-6-phosphate and cofactor NAD+ is added in the appropriate buffer. The rate of change in the absorbance at 340 nm is measured and is directly proportional to the level of drug metabolite in the test sample.

Another reporter for this assay is a thermostable adenylate kinase. Test antibody specific for the class of drug of interest is immobilised onto a solid-phase. The solid-phase is treated to prevent further non-specific binding thereto. The solid-phase is washed with wash buffer, which may or may not contain detergent. A urine test sample is added along with the drug-adenylate kinase (AK) conjugate. The drug-AK conjugate is thermostable and is not active when bound to the antibody immobilised to the solid-phase.

The sample is then incubated, e.g.: 37° C. for 60 mins. The contents of the micro-titre well is then removed and endogenous ATP removed by addition of adenosine-5'-triphosphatase or apyrase and incubation at 37° C. The sample is then heated to 90° C. to inactivate any mesophilic adenylate kinase present.

Adenosine diphosphate (ADP) is added and the temperature is maintained at 90° C. such that the thermostable adenylate kinase can convert the ADP to ATP. This incubation generates ATP exclusively from thermostable adenylate kinase. The ATP generated is then assayed by conventional ATP bioluminescence using a luciferin/luciferase system. Signal from contaminating adenylate kinase in the luciferin/luciferase may be quenched by the addition of a specific enzyme inhibitor. The ATP bioluminescence measured is directly proportional to the concentration of the drug metabolite in the original test sample.

Other solid-phases are suitable, such as latex or magnetic bead, and the test sample may be sera or other body fluid.

Example 6

Assays for the Detection of Human Papilloma Virus DNA

Assay A: Cervical cells are collected and resuspended in phosphate buffered saline. PCR amplification of the HPV16, or equivalent sequence, is carried out as described in Lambropoulous et al. (1994) Journal of Medical Virology: 43, 228–230 using the consensus primers MY11 and MY09 and 30 rounds of amplification.

The PCR products are then transferred and immobilised on to a non-charged nylon coated microtitre plate, or equivalent. An oligonucleotide probe specific for HPV16 (MY14) conjugated to a thermostable adenylate kinase is then added and incubated. The oligonucleotide-AK conjugate is prepared following an identical method described the synthesis of DNA-antibody conjugates. This complex comprises of a biotinylated AK and an avidin-biotinylated DNA complex generated using available methodology: Ruzicka et al. Science 1993, 260, 698–699.

Non-bound material is then removed by washing and any endogenous ATP present on the solid-phase is removed by the addition of adenosine-5'triphosphatase or apyrase. The solid-phase is then washed and the sample heated to 90° C., or equivalent, to denature and inactivate any mesophilic adenylate kinase that may be present.

Adenosine diphosphate (ADP) is added and the temperature is maintained at 90° C. such that the thermostable adenylate kinase can convert the ADP to ATP. This incubation generates ATP exclusively from thermostable adenylate kinase. The ATP generated is then assayed by conventional ATP bioluminescence using a luciferin/luciferase reaction. A positive signal is indicative of HPV infection.

Assay B: Cervical cells are collected and fixed onto a solid-surface, a non-charged nylon membrane contained within a microtitre plate. The cells are lysed and the endogenous ATP present on the solid-phase is removed by the addition of adenosine-5'-triphosphatase or apyrase. An oligonucleotide probe specific for HPV16 (MY14: 5'CATACACCTCCAGCACCTAA3') conjugated to a thermostable adenylate kinase is then added. The oligonucleotide-AK conjugate is prepared following an identical method described the synthesis of DNA-antibody conjugates. This complex comprises a biotinylated AK and an avidin-biotinylated DNA complex generated using available methodology: Ruzicka et. al. Science 1993, 260, 698–699.

After incubation, 37° C. for 60 min, the sample is heated to 90° C., or equivalent, to denature and inactivate any mesophilic adenylate kinase that may be present. ADP added and the temperature is maintained at 90° C. such that the thermostable adenylate kinase can convert the ADP to ATP. This incubation generates ATP exclusively from thermostable adenylate kinase. The ATP generated is then assayed by conventional ATP bioluminescence using a luciferin/luciferase reaction. A positive signal is indicative of HPV infection.

Example 7

An Assay to Screen Peptide Combinational Libraries

Peptides are synthesised on small beads (100 μl–200 μm) using standard solid-phase peptide synthesis methodology. The sequence corresponds to a combinational peptide library generated as described Lam. et al. (1991) Nature (UK). 354, 82–84.

The beads are split into 20 portions and a separate amino acid coupled to each portion. The beads are then recombined, randomised, and split into 20 for addition of the next amino acid. This process is repeated to build a peptide library of all possible combinations of amino acids. In theory each bead should have a different peptide sequence attached. After synthesis the beads are washed and any endogenous ATP is removed by addition of adenosine-5'-triphosphatase or apyrase. A ligand-thermostable AK conjugate is added and the sample heated to 90°, or equivalent, to denature and inactivate any mesophilic adenylate kinase that may be present.

Adenosine diphosphate (ADP) is added and the temperature is maintained at 90° C. such that the thermostable adenylate kinase can convert the ADP to ATP. The beads are split into portions and screened for the generation of light generated by a luciferin/luciferase reaction using a standard luminescence reader. Portions generating a positive signal are split into further portions and re-screened. This process is continued using a microscope equipped with a charge couple device camera, until the signal from a single bead is identified. The bead is removed and the sequence of peptide is then determined using standard micro-sequencing methodology.

Example 8

An Assay for Botulinum Toxin

Antibody specific for the botulinum toxin is immobilised onto a solid-phase. The solid-phase may be a microtitreplate but other solid-phases are suitable, such as latex or magnetic bead. The solid-phase is treated to prevent further non-specific binding thereto. The solid-phase is washed with wash buffer, which may or may not contain detergent. Test sample is added. The test sample is a food sample, but may be whole blood or body fluid. The sample is then incubated, e.g.: 37° C. for 60 mins, allowing the free toxin in the sample to bind capture antibody. The solid-phase is then washed to remove non-specifically bound material and an antibody specific for the botulinum toxin is added to which a thermostable adenylate kinase reporter enzyme has been conjugated. This antibody may be a polyclonal or a monoclonal antibody. The conjugate is then incubated at 37° C. for 60 minutes, or equivalent.

Non-bound material is then removed by washing and any endogenous ATP present on the solid-phase is removed by the addition of adenosine-5'-triphosphatase or apyrase. The solid-phase is washed and the sample heated to 90° C., or equivalent, to denature and inactivate any mesophilic adenylate kinase that may be present.

Adenosine diphosphate (ADP) is added and the temperature is maintained at 90° C. such that the thermostable adenylate kinase can convert the ADP to ATP. This incubation generates ATP exclusively from thermostable adenylate kinase. The ATP generated is then assayed by conventional ATP bioluminescence using a luciferin/luciferase reaction. Signal form contaminating adenylate kinase in the luciferin/luciferase may be quenched by the addition of a specific enzyme inhibitor. The ATP bioluminescence measured is directly proportional to the concentration of the toxin in the original test sample.

The invention thus provides method and apparatus for a sensitive capture-type assay.

REFERENCES

Gould S J and Subramini S (1988) Firefly luciferase as a tool in molecular and cell biology. Anal. Biochem. 175: 5–13.

Kricka L J (1993) Ultrasensitive immunoassay techniques. Clin. Biochem. 26: 325–331.

Ki W-K and Takahisa O (1988) Purification and characterisation of adenylate kinase from extreme thermophile *Thermus caldophilius* GK24. Korean J. Appl. Microbiol. Bioeng. 16: 393–397.

Lacher K and Schäfer G. (1993) Archaebacterial adenylate kinase from the thermoacidophile *Sulfolobus acidocaldarius*: purification, characterization and partial sequence. Arch. Biochem. Biophys. 302: 391–397.

Rusnak P, Haney P and Konisky J (1995) The adenylate kinases from a mesophilic and three thermophilic methanogenic members of the archaea. J. Bacteriol. 177: 2977–2981.

Bonisch H, Backmann J, Kath T, Naumann D and Schäfer G (1996) Adenylate linase from *Sulfolobus acidocaldarius*: expression in *Escherichia coli* and characterization by Fourier transfrom infrared spectroscopy. Arch. Biochem. Biophys. 333: 75–84.

What is claimed is:

1. An assay for an analyte, comprising contacting the analyte with a thermostable reporter adenylate kinase coupled to a binding agent specific for the analyte, wherein a complex is formed, adding ADP and testing for formation of ATP wherein, prior to the addition of ATP, endogenous kinase and uncomplexed thermostable reporter adenylate kinase is substantially removed by washing and, residual endogenous kinase is inactivated by heating, wherein the amount of said ATP formed correlates to the concentration of the analyte.

2. The assay of claim 1, wherein the amount of thermostable reporter adenylate kinase complexed with the analyte is substantially proportional to the amount of analyte.

3. The assay of claim 1, wherein formation of ATP is measured using luciferin/luciferase.

4. An assay for determining the presence and/or amount of an analyte in a sample, comprising exposing the sample to a thermostable reporter adenylate kinase coupled to a binding agent specific for the analyte, so that the reporter adenylate kinase is specifically associated with any analyte present in the sample via the binding agent; removing thermostable reporter adenylate that is not bound to analyte; exposing said thermostable reporter adenylate kinase bound to the analyte to ADP; and testing for formation of ATP, wherein prior to addition of ADP, residual kinase other than thermostable reporter adenylate kinase is substantially removed by heating.

5. The assay of claim 1, comprising further adding an ATPase to the analyte and removing the ATPase from the analyte prior to adding ADP.

6. The assay of claim 5, wherein the ATPase is inactivated by heating the ATPase.

7. An assay for determining presence and/or amount of an analyte in a sample comprising:

exposing the sample to a detector compound, the detector compound comprising an antibody specific to the analyte coupled to a thermostable enzyme; isolating (i) detector compound that has specifically bound to analyte from (ii) detector compound that has not specifically bound to analyte; determining the presence and/or amount of detector compound that has bound to analyte by adding a substrate for the thermostable enzyme and measuring a product formed by conversion of said substrate to said product by said thermostable enzyme; therein prior to adding the substrate non-thermostable enzymes are destroyed by application of heat.

8. The assay of claim 7, wherein the enzyme is adenylate kinase and the substrate is ADP, the ADP is converted into ATP by the thermostable enzyme.

9. The assay of claim 8, wherein background ATP compound is removed by the addition of ATPase prior to adding ADP.

10. An assay for an analyte, comprising the steps:
(a) specifically binding the analyte with a thermostable reporter kinase which has been coupled to a binding agent specific for the analyte forming a complex;
(b) washing to remove endogenous-non-thermostable kinase and thermostable reporter kinase not bound to analyte;
(c) heating to inactivate endogenous kinase not removed by step (b); and
(d) adding ADP and testing for formation of ATP.

* * * * *

UNITED STATES PATENT AND TRADEMARK OFFICE
CERTIFICATE OF CORRECTION

PATENT NO. : 6,913,896 B1
DATED : July 5, 2005
INVENTOR(S) : Raven et al.

It is certified that error appears in the above-identified patent and that said Letters Patent is hereby corrected as shown below:

Column 18,
Line 57, the abbreviation "ATP", immediately following the words "addition of", should be deleted and replaced with the abbreviation -- ADP --.

Column 19,
Line 7, the word -- kinase -- should be inserted immediately after the word "adenylate".

Column 20,
Line 5, the word "therein" should be deleted and replaced with the word -- wherein --.

Signed and Sealed this

First Day of November, 2005

JON W. DUDAS
*Director of the United States Patent and Trademark Office*